United States Patent [19]

Kurtz et al.

[11] Patent Number: 4,468,226
[45] Date of Patent: Aug. 28, 1984

[54] SURGICAL DRAINAGE APPARATUS WITH INCREMENTAL SUCTION CONTROL AND INDICATION

[75] Inventors: Leonard D. Kurtz, Woodmere; Joseph M. LiCausi, Port Jefferson Station, both of N.Y.

[73] Assignee: BioResearch Inc., Farmingdale, N.Y.

[21] Appl. No.: 386,436

[22] Filed: Jun. 8, 1982

[51] Int. Cl.³ .............................................. G01L 21/00
[52] U.S. Cl. .................................. 604/321; 604/318; 73/714; 137/205; 137/212
[58] Field of Search ................................. 604/317–321, 604/247, 133; 251/340; 137/625.3, 625.33, 205, 212; 116/268, 272, 264, 266, 270, 277, DIG. 7, DIG. 8, DIG. 24, DIG. 25

[56] References Cited

U.S. PATENT DOCUMENTS 3,363,626  1/1968  Bidwell et al. ...................... 604/321
4,396,386  8/1983  Kurtz et al. ........................ 604/319

*Primary Examiner*—Charles Frankfort
*Assistant Examiner*—Willie Morris Worth
*Attorney, Agent, or Firm*—Larson and Taylor

[57] ABSTRACT

A surgical drainage unit is provided for draining fluids from the body of a patient wherein the suction pressure, applied through a suction inlet of the unit to draw fluids into the unit, is incrementally controlled and a direct indication of the applied suction pressure is afforded. A device which contracts responsive to an increase in suction in a collection chamber of the unit is equipped with an indicator vane that cooperates with a fixed scale to indicate the amount of movement of the bellows and hence indicate the suction within the collection chamber. A manually adjustable control valve incrementally controls the amount of air admitted to a suction line within the unit to thereby control the applied suction. A negative pressure relief valve is also provided so that excess negativity within the inlet tube can be manually relieved.

15 Claims, 14 Drawing Figures

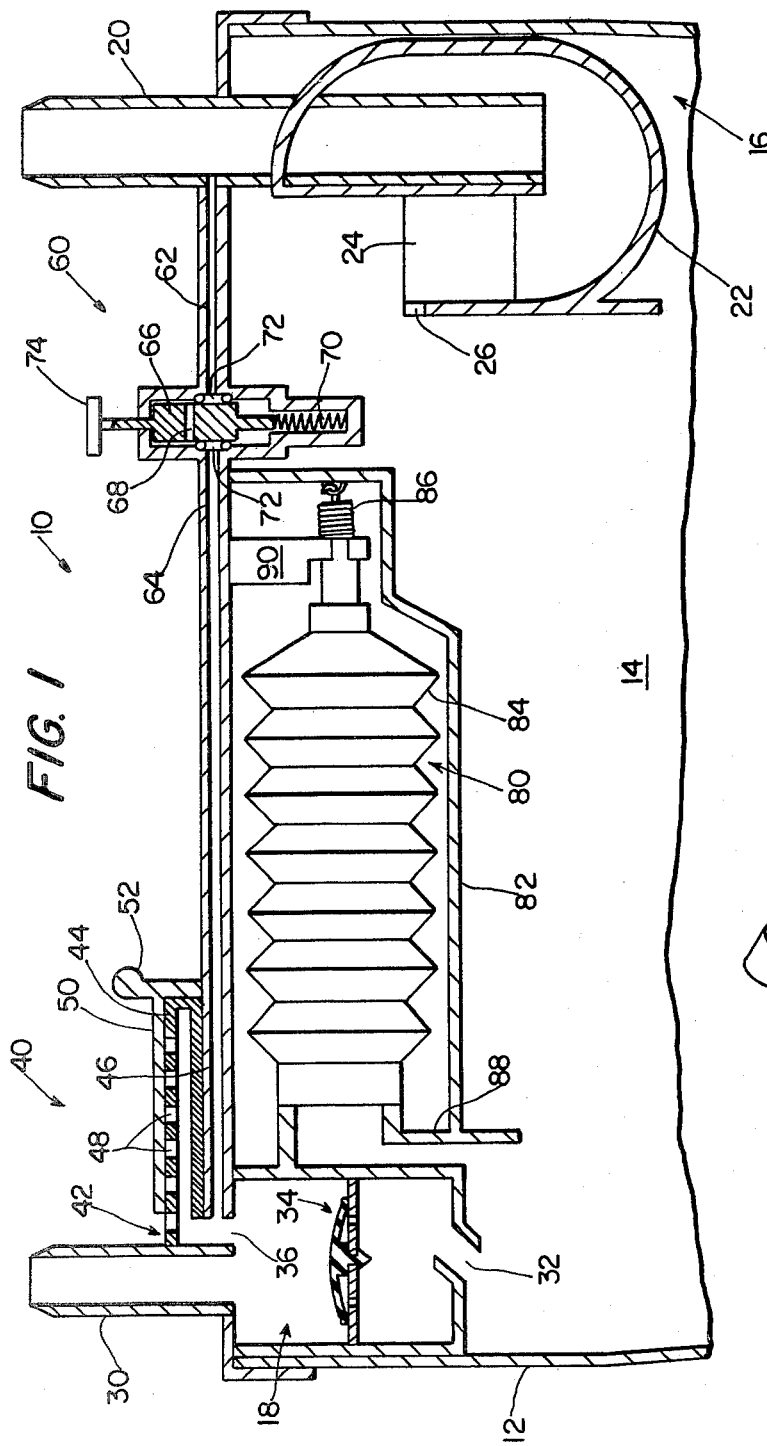
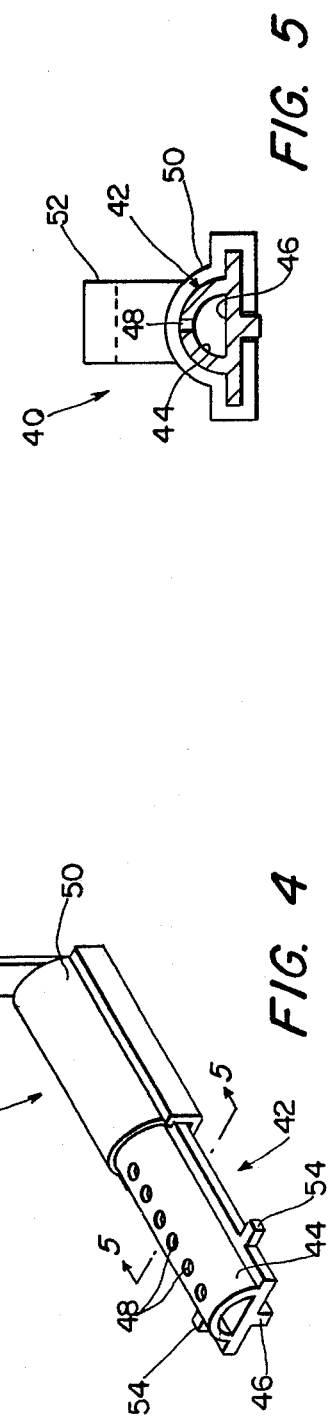

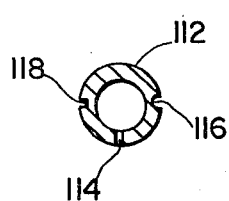
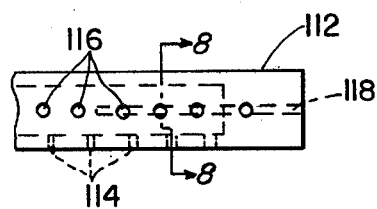
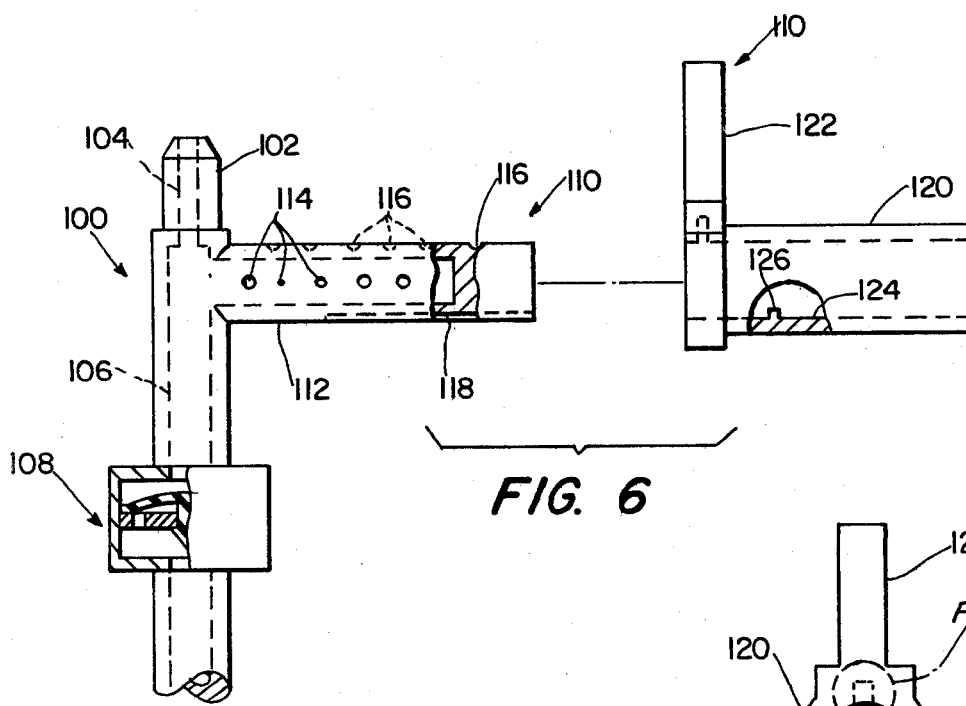
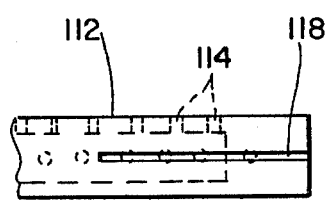
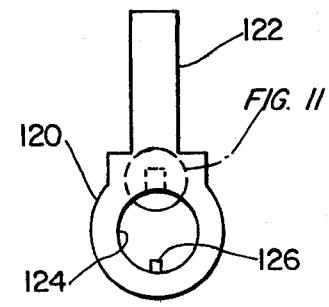
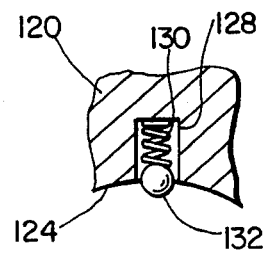

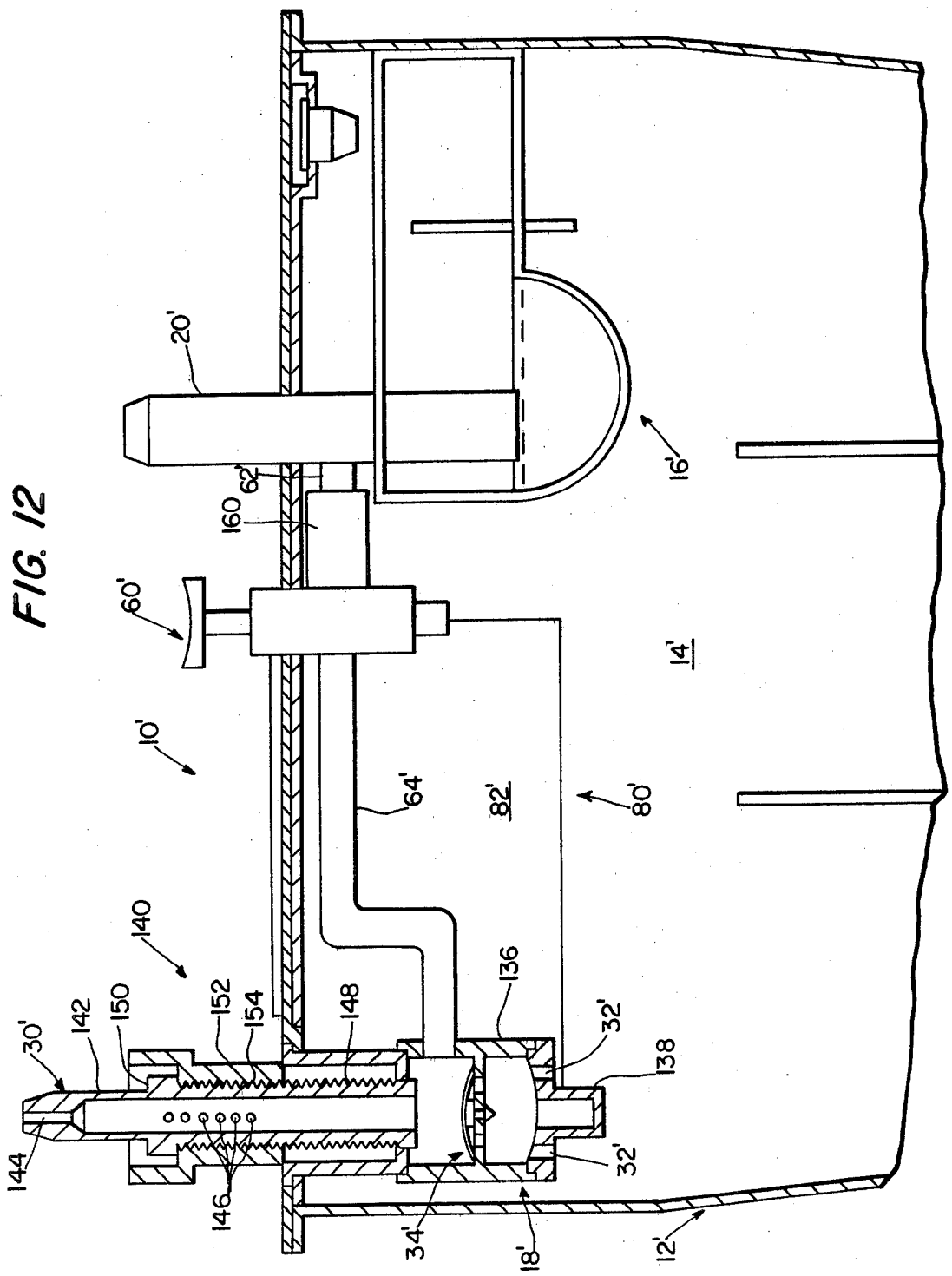

SURGICAL DRAINAGE APPARATUS WITH INCREMENTAL SUCTION CONTROL AND INDICATION

FIELD OF THE INVENTION

The present invention relates to surgical drainage devices used in draining fluids from the body, e.g. the pleural cavity, and is particularly concerned with an improved drainage apparatus which provides ready incremental control and indication of the applied suction pressure.

BACKGROUND OF THE INVENTION

It is essential for normal breathing that the space within the pleural cavity surrounding the lungs be free of liquid and be subject to a negative pressure so as to draw the lungs outwardly to fill this pleural cavity in order to permit proper breathing. Any invasion of the pleural cavity such as caused by lung surgery or foreign objects which pierce the rib cage or such as occur, for example, where the patient has pleurisy, generates fluids in the pleural cavity which tend to obstruct normal breathing by preventing full expansion of the lungs. It is necessary to provide a device which can remove these fluids from the pleural cavity and at the same time ensure that the desired degree of negative pressure imposed by the suction control chamber is approximately maintained within the pleural cavity so that the lung maintains its maximal expansion.

Two of the basic types of apparatus which have been used for this purpose are shown, for example, in U.S. Pat. Nos. 3,363,626 and 3,363,627, and in pending U.S. application Ser. No. 120,295 filed Feb. 11, 1980, which are herein incorporated by reference. The first of these apparatuses provides three chambers, one chamber comprising a collection chamber for collecting the fluids drained from the pleural cavity through a thoracotomy tube, a second chamber known as an underwater seal chamber which protects the pleural cavity from being subject to atmospheric pressure, and a third chamber known as a suction control chamber which serves to regulate the degree of negative pressure within the pleural cavity. The other of these apparatuses provides a collection chamber with an underwater seal chamber located at the upper end thereof adjacent the lower end of the thoracotomy tube. Secretions from the body cavity form the underwater seal and excess secretions thereafter overflow into the collection chamber. These types of apparatuses have been highly successful in both removing fluids from the pleural cavity and in maintaining the desired degree of negativity within the pleural cavity.

It has been found that nurses frequently will "milk" the thoracotomy tubes in an effort to remove any clots or obstructions from the tube. This "milking" of the tube is achieved by squeezing the flexible thoracotomy tube adjacent the upper end and drawing the fingers down the tube to cause the fluids within the tube to be passed out the lower end of the tube and into the collection chamber. Obviously, this action has the effect of substantially lowering the degree of negativity within the pleural cavity. Such high negativity can be damaging to the pleural cavity and may also cause the liquid within a combined water seal-collection chamber to be drawn up into the pleural cavity. In addition, the entire water seal can be lost into the pleural space or the collection chamber during periods of high negativity in the pleural cavity. The loss of the water seal has the potential for causing pneumothorax in the event that the suction becomes disconnected. Thus, there is need for a means of providing necessary relief for the condition of excess negativity in the pleural cavity.

In one of the applicant's pending U.S. application Ser. No. 256,152, a metered air pump is disclosed by which excess negative pressure can be relieved by pumping as many small units of air into the thoracotomy tube as necessary. In another of applicant's pending U.S. application Ser. No. 309,796, an automatically operated valve connects the thoracotomy tube directly with the atmosphere whenever excess negativity occurs.

When excess negativity is relieved in the collection chamber and/or the thoracotomy tube, it is important that the pressure in the collection chamber and/or the thoracotomy tube be prevented from reaching atmospheric pressure. Should the pressure in the collection chamber and/or the thoracotomy tube reach atmospheric pressure, the collection chamber immediately ceases to drain fluids from the pleural cavity, a pneumothorax develops, the lung collapses and breathing of the patient can quickly become difficult. So long as the collection chamber and/or the thoracotomy tube are subatmospheric, a pneumothorax does not occur.

Even though drainage devices have been developed which do not require a filling of the underwater seal chamber (see also, for example, U.S. Pat. Nos. 4,015,603 and 4,312,351), these devices generally do not provide a direct indication of the suction force being exerted. Such a feature is, of course, highly desirable in a drainage device.

SUMMARY OF THE INVENTION

In accordance with the present invention, an improved medical drainage device for draining fluids from the body of a patient is provided which enables the operator to incrementally control the suction being applied and which affords a direct indication of the suction pressure being applied to the suction chamber so the applied suction can be closely controlled. The suction pressure control and indicator arrangement is simple and rugged in construction and efficient and dependable in use. According to the invention, the surgical drainage apparatus comprises a container which is connected to a suction source so that fluids can be drawn into the container, a fluid inlet in the container, a collection chamber for collecting the fluids drawn into the container through the fluids inlet, a manually adjustable, incrementally variable control device for controlling the amount of suction created within the container, and an indicator arrangement responsive to the suction pressure created within the collection chamber for providing an indication of the applied suction. The apparatus of the invention is completely "dry" prior to use, i.e., does not require any prefilling by a user.

In a preferred embodiment of the invention, the basic component of the indicator arrangement is a bellows which is connected to the collection chamber of the drainage device and which contracts with increased suction in the collection chamber. A scale cooperates with a pointer or indicator attached to the bellows to provide an indication of the suction. In this preferred embodiment, the controllable, incrementally variable control device comprises a control valve which is connected to a suction line and which incrementally controls the amount of air supplied to the suction line and hence the suction pressure in the container. An air flow control sheath associated with the control valve enables the operator to "set" the desired pressure, and thus with the direct reading of the applied suction pressure provided by the indicator arrangement to the operator during adjustment of the sheath the suction can be closely monitored and controlled. A negative pressure relief valve which fluidly connects the suction line and the fluid inlet allows excess negative pressure in the inlet tube to be quickly relieved.

Other features and advantages of the invention will be set forth in, or apparent from, the detailed description of a preferred embodiment found hereinbelow.

BRIEF DESCRIPTION OF THE DRAWINGS

FIG. 1 is a cross-sectional front view of a drainage apparatus according to the present invention.

FIG. 4 is a perspective view of the incremental suction control of the present invention.

FIG. 5 is a cross-sectional view of the suction control depicted in FIG. 4.

FIG. 6 is a front elevation view of an alternative embodiment of a suction control.

FIG. 7 is a partial top plan view of the suction control depicted in FIG. 6.

FIG. 8 is a cross-sectional view taken along the line 8—8 in FIG. 7.

FIG. 9 is a partial bottom view of the suction control depicted in FIG. 6.

FIG. 10 is a side elevation view of the sheath depicted in FIG. 6.

FIG. 11 is a cutaway view of a portion of the sheath depicted in FIG. 10.

FIG. 12 is a cross-sectional front view of an alternative embodiment of a drainage apparatus according to the present invention.

DESCRIPTION OF THE PREFERRED EMBODIMENTS

Figures 2, 3:
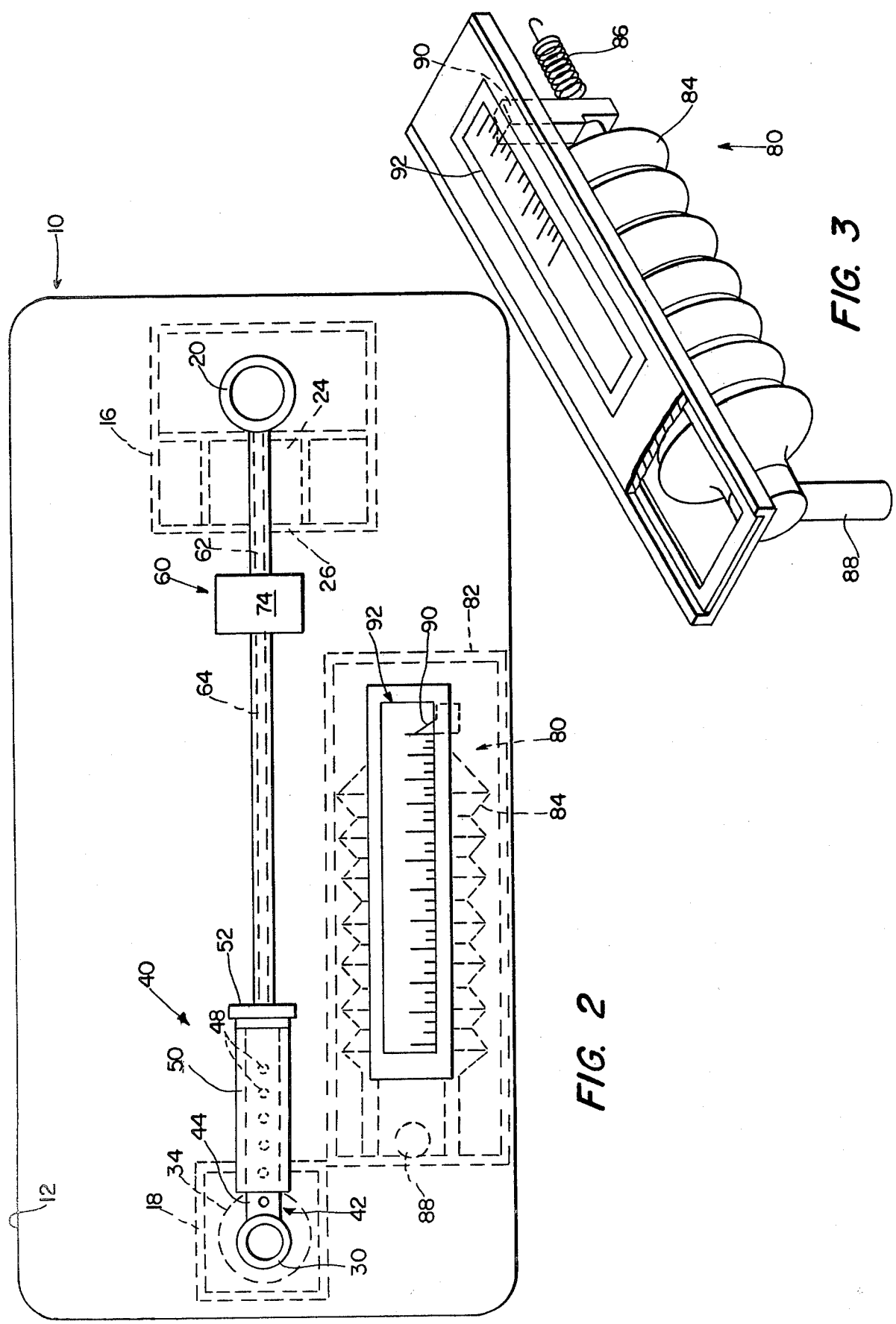
FIG. 2 is a top view of the drainage apparatus depicted in FIG. 1.
FIG. 3 is a perspective view of the suction indicator of the present invention.

With reference now to the drawings in which like numerals represents like elements throughout the several views, a preferred embodiment of a drainage device 10 is depicted in FIGS. 1 and 2. Drainage device 10 comprises a housing 12 having a main collection chamber 14, a fluid seal chamber 16, and a suction control chamber 18. Collection chamber 14 merely comprises a container formed at the bottom of housing 10 for the collection of fluids drawn or sucked in by the drainage device 10 and need not be additionally described. Further, fluid seal chamber 16 is of the type described in commonly assigned U.S. Pat. No. 4,312,351 (Kurtz et al), the subject matter of which is hereby incorporated by reference, and reference is made to that patent for a more complete description of this feature. However, for the sake of completeness, fluid seal chamber 16 will also be briefly described here, together with suction control chamber 18.

Fluid seal chamber 16 includes therein a portion of an inlet tube 20 which extends through housing 12 and which is adapted to be connected to the patient through a throacotomy tube (not shown). The bottom of fluid seal chamber 16 is formed into a cup portion 22 into which inlet tube 20 opens. An opening 24 on one side of fluid seal chamber 16 allows the fluids collected in cup portion 22 to flow out over a ledge 26 and into main collection chamber 14.

Suction control chamber 18 includes an outlet tube 30 which is adapted to be connected to a suitable source of suction. An angled passageway 32 connects suction control chamber 18 with main collection chamber 14. Disposed between outlet tube 30 and angled passageway 32 is an umbrella valve means 34. Umbrella valve means 34 acts as a one way valve to permit the flow of fluids from main collection chamber 14 to outlet tube 30, but to prevent any reverse flow. Located near the top of suction control chamber 18 adjacent outlet tube 30 is an opening 36. Fluidly connected to opening 36 is a variable control means 40.

As shown in greater detail in FIGS. 4 and 5, variable control means 40 includes a tubular body 42 having a semicircular top portion 44 and a T-shaped bottom portion 46. Located along the top of semicircular portion 44 is a series of holes 48. Slidably mounted on tubular body 42 is a sheath 50 having a handle 52. As clearly shown in FIG. 5, sheath 50 completely surrounds tubular body 42 except for the lower extending portion of T-shaped portion 46 with which tubular body 42 is attached to the top of housing 12. T-shaped portion 46 also includes stops 54 so that sheath 50 can slide along tubular body 42 to a position where all of the holes except the first are completely covered by sheath 50.

Provided on top of housing 12 is a negative pressure relief valve 60. Relief valve 60 is connected on one side by a small passage 62 to inlet tube 20 and by a larger passageway 64 to opening 36. As shown best in FIG. 1, relief valve 60 includes a piston body 66 with an aperture 68 therethrough. Piston body 66 is normally held in the position depicted in FIG. 1 by a spring 70 acting on the bottom of piston body 66 so that aperture 68 is not aligned with passageways 62 and 64. O-ring 72 seals piston body 66 from passageways 62 and 64. Relief valve 60 includes a handle 74 which can be depressed to align aperture 68 with passageways 62 and 64.

As shown in FIGS. 1, 2 and 3, the suction indicating means 80 is located in a chamber 82 which is open to atmosphere. Suction indicating means 80 includes a bellows 84 mounted in chamber 82 which is connected through a spring 86 to one end wall of chamber 82. The other fixed end of bellows 84 is supported in chamber 82 by an L-shaped inlet tube 88. Inlet tube 88 is mounted along the other end wall of chamber 82. Inlet tube 88 opens into main collection chamber 14 and the interior of bellows 84 which is sealingly mounted to L-shaped inlet tube 88. The movable end of bellows 84 includes an indicator vane 90 mounted thereon which cooperates with a scale 92 provided on the upper wall of chamber 82 to indicate the imposed suction. In practice, in an exemplary embodiment under consideration, the imposed suction will vary from about −10 cm of water to about −100 cm of water. As chamber 82 is at atmospheric pressure, bellows 84 contracts when suction is applied therein through inlet tube 88. The amount of contraction is proportional to the applied suction and thus indicator vane 90 in cooperation with scale 92 provides a direct reading of the suction applied to main collection chamber 14 and the unit.

It is noted that the wall suction in a hospital or like facility is frequently set at a "wide open" setting and typically varies between 200 mm Hg and 750 mm Hg deadhead. This amount of suction can obviously cause problems in a drainage device, and to overcome these problems and permit the device of the invention to be directly connected to wall suction without controlling or modifying the latter, a restriction (not shown) is conveniently provided in outlet tube 30. This restriction is sized so that with control means 40 wide open (maximum air), the imposed suction will be about −10 cm of water. Obviously, other suction levels can be chosen as desired. This restriction in conbination with control means 40 provides a range discussed above, i.e., from about −10 cm of water to about −100 cm of water. It has been found that for a quarter inch (0.250 inch diameter) outlet tube, satisfactory results have been obtained where the size of the restriction ranges between about 0.050 inches and 0.187 inches. In general, the restriction provided should not be so great that, with control means 40 wide open, the desired minimum negativity cannot be achieved.

In operation, drainage device 10 functions in the following manner. Initially, inlet tube 20 is connected to the area of the patient to be drained and outlet tube 30 is connected to a suitable source of suction. The fluids collected from the patient through inlet tube 20 first fill fluid seal chamber 16 up to ledge 26 and then the fluids spill over into main collection chamber 14. As soon as the suction is connected to outlet tube 30, suction indicating means 80 immediately indicates the applied suction in main collection chamber 14 due to the movement of vane 90 relative to scale 92. The movement of vane 90 occurs as bellows 84 contracts under the applied suction in main collection chamber 14 against the force of spring 86. Depending on the reading of vane 90, variable control means 40 is adjusted to provide the negative pressure desired in collection chamber 14. Initially, variable control means 40 is adjusted so that sheath 50 covers all but the first hole in tubular body 42. Depending upon the suction pressure desired, sheath 50 is moved by pushing on handle 52 to uncover additional holds 48. In this manner, the suction pressure in main collection chamber 14 is incrementally adjusted as more holes 48 are uncovered.

In one embodiment of the present invention, the first hole only is open and provides a suction pressure of −100 cm of water. As additional holes are uncovered, the applied suction pressure in collection chamber 14 varies as follows: the first two holes open, minus 75 cm of water; first three holes open, minus 50 cm of water; first four holes open, minus 35 cm of water; first five holes open, minus 20 cm of water; and all six holes open, minus 10 cm of water. Obviously, a greater or lesser number of holes and the size of the holes can be varied to change the incremental pressures achieved by uncovering a set number of holes.

Should an excess negative pressure be created in the inlet tube 20, the fluid in fluid seal chamber 16 rises in inlet tube 20. As this is not desired, upon seeing the fluid in inlet tube 20, negative pressure relief valve 60 is actuated. By actuating relief valve 60, the controlled and desired suction pressure in suction control chamber 18 is fluidly connected to inlet tube 20. In this manner, the excess negative pressure in the thoracotomy tube is relieved as air is bled into inlet tube 20. It should be noted that small passageway 62 restricts the flow of air sufficiently so that where a short period of excess negativity is desired in inlet tube 20, this desired excess negativity is not immediately relieved. However, prolonged periods of undesired excess negativity are relieved.

Depicted in FIGS. 6 to 11 is an alternative embodiment of a suction control chamber 100. In this embodiment, an outlet tube 102 is provided with a restricted outlet passageway 104 and a larger passageway 106 in which an umbrella valve means 108 is located. Fluidly connected to larger passageway 106 above umbrella valve means 108 is a variable control means 110. Variable control means 110 includes a tubular body 112 with a closed outer end. As additionally shown in FIGS. 7, 8 and 9, a series of holes 114 is provided in tubular body 112. Hole 114 closest to outlet tube 102 is the largest of holes 114 while the second hole is the smallest of holes 114. The third and succeeding holes 114 are successively larger than the preceding hole. Tubular body 112 also includes a series of notches 116 located along the top outer surface of tubular body 112. Located along the bottom outer surface of tubular body 112 starting at the outer end thereof is an elongate slot 118.

With reference now to FIGS. 10 and 11 as well as FIG. 6, a sheath 120 for tubular body 112 is depicted. Sheath 120 includes a handle 122 and a cylindrical bore 124 with a closed end. Bore 124 is sized to snugly receive tubular body 112 such that sheath 120 is capable of sliding relative thereto. Upstanding from the bottom of bore 124 is a small peg 126. As sheath 120 slides onto tubular body 112, peg 126 is received in slot 118 to prevent sheath 120 from rotating relative to tubular body 112. Located in the top of bore 124 is a recess 128. Housed in recess 128 is a spring 130 which urges a ball 132 into bore 124. As sheath 120 is received on tubular body 112, ball 132 is pushed upward against the force of spring 130 into recess 128. As peg 126 prevents sheath 120 from rotating, ball 132 is positioned such that ball 132 resiliently engages notches 116 as sheath 120 advances along tubular body 112. Notches 116 are positioned such that ball 132 enters a respective notch 116 when a predetermined number of holes 116 are opened to atmosphere and not covered by sheath 120. In this manner, sheath 120 is easily positioned by handle 122 to a position where a desired number of holes 114 are exposed to atmosphere, and ball 132 resiliently engages the respective notch 116 to indicate the desired positioning of sheath 120 and to resiliently hold sheath 120 in place.

It should be noted that holes 114 vary in size from a very small second hole to a large last hole which is approximately the same size as the first hole. By providing holes 114 of different sizes, a more evenly distributed range of desired suction pressures are maintained in the collection chamber. Obviously, a greater number of holes can be provided for a greater increment of control over the suction pressure in the collection chamber.

Depicted in FIG. 12 is an alternative embodiment of a drainage device 10′ comprising a housing 12′ having a main collection chamber 14′, a fluid seal chamber 16′, and a suction control chamber 18′. Main collection chamber 14′ and fluid seal chamber 16′ having an inlet tube 20′ are similar to main collection chamber 14 and fluid seal chamber 16 described above and will not be discussed further.

Suction control chamber 18′ is similar in function to suction control chamber 18 and includes an outlet tube 30′ connected to a housing 136 in which an umbrella valve means 34′ is located. Located in this embodiment of housing 136 is a well 138. Should housing 12′ be tipped allowing liquids to enter housing 136 through passageways 32', a portion of the liquids entering housing 136 will remain in well 138 and indicate that drainage device 10 has been tipped.

In this embodiment of the present invention, outlet tube 30' forms a portion of a variable control means 140 having a tubular body 142. One end of tubular body 142 is attached to housing 136 and the other end contains a restricted outlet 144. Disposed along a portion of the length of tubular body 142 are a series of holes 146. Tubular body 142 also has an externally threaded portion 148 which terminates at a stop 150. Surrounding tubular body 142 is a sheath 152 having an internally threaded portion 154 which mates with threaded portion 148 of tubular body 142. With this construction, sheath 152 is threadably received on tubular body 142 so that rotation of sheath 152 results in longitudinal movement of sheath 152 along tubular body 142. As sheath 152 is turned in one direction, holes 146 can be incrementally uncovered while rotation of sheath 152 in the other direction results in the incremental covering of holes 146. It should be noted that stop 150 prevents sheath 152 from advancing along tubular body 142 to a position where the uppermost hole 146 is covered.

Similar to drainage device 10, drainage device 10' is provided with a negative pressure relief valve 60' which is connected on one side by passageway 62' to inlet tube 20' and on the other side by passageway 64' to suction control chamber 18'. However, in this embodiment, a one-way "pop" valve 160 is disposed between negative pressure relief valve 60' and passageway 62'. One-way valve 160 permits fluid flow only from suction control chamber 18' to inlet tube 20' to relieve excess negative pressure in inlet tube 20'.

Figure 14:
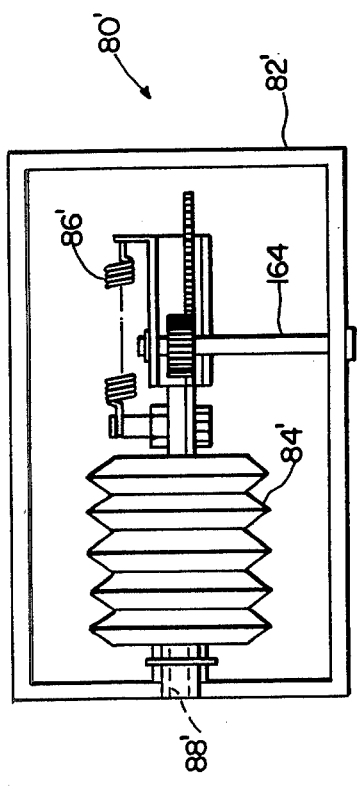
FIG. 14 is a cross-sectional rear view of the suction indicator depicted in FIG. 13.
Figure 13:
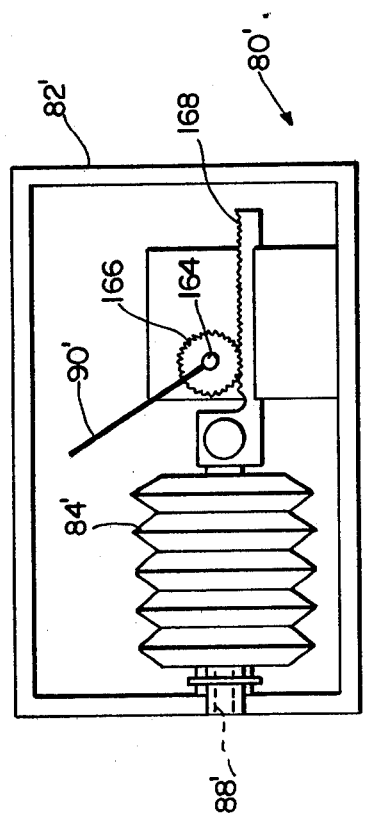
FIG. 13 is a cross-sectional top view of an alternative embodiment of a suction indicator.

As shown in greater detail on FIGS. 13 and 14, drainage device 10' is provided with a suction indicating means 80' which is similar to suction indicating means 80 described above. Suction indicating means 80' includes a chamber 82', a bellows 84', a spring 86', and an inlet tube 88'. In this embodiment, an indicator vane 90' is rotatably mounted to chamber 82' on a stem 164. Mounted to stem 164 is a gear 166 which meshes with a rack 168 attached to the end of bellows 84'. With this construction, the expansion or contraction of bellows 84' causes the longitudinal movement of rack 168 which in turn rotates gear 166 and indicator vane 90'. Indicator vane 90' is located adjacent a scale and indicates the suction in collection chamber 14'.

The operation of drainage device 10' is similar to the operation of drainage device 10 described above and need not be discussed further.

Although the invention has been described relative to exemplary embodiments thereof, it will be understood that variations and modifications can be effected in these embodiments without departing from the scope and spirit of the invention.

We claim:

1. A surgical drainage apparatus for draining fluids from the body of a patient, said apparatus comprising:
    a container;
    a fluid inlet in said container;
    a collection chamber formed in said container for collecting fluids received through said fluid inlet;
    connection means for connecting said container to a suction source so as to create a suction within said container and thereby draw fluids into said container through said fluid inlet;
    manually adjustable, incrementally variable control means for incrementally controlling the amount of suction created within the collection chamber of said container;
    indicator means, located within said container and responsive to the suction created within said collection chamber, for providing an indication of the suction created; and
    an underwater seal provided between said fluid inlet and said connection means and a manually actuatable negative pressure relief valve means for fluidly connecting said connection means and said fluid inlet such that excess negative pressure in said fluid inlet is relieved by actuation of said relief valve means.

2. A surgical drainage apparatus as claimed in claim 1 wherein said variable control means includes an elongate tubular body fluidly connected to said connection means, a plurality of openings located along the length of said tubular body, and a sheath means which covers said openings and which is slidably movable along said body to uncover a select number of said openings so as to bleed air to said connection means to incrementally control the suction within said collection chamber.

3. A surgical drainage apparatus as claimed in claim 2 wherein said connection means comprises means defining a passageway for suction air between said collection chamber and a suction inlet whereby said control means selectively bleeds atmospheric air to said passageway to control the suction created in said collection chamber.

4. A surgical drainage apparatus as claimed in claim 3 wherein said variable control means includes a stop means which prevents said sheath means from moving to a position where all of said openings are covered.

5. A surgical drainage apparatus as claimed in claim 4 wherein said variable control means further includes a positioning means for selectively positioning and retaining said sheath means at a plurality of positions corresponding to the various uncovering positions for said plurality of openings.

6. Apparatus as claimed in claim 1 wherein said indicating means comprises a pressure responsive device disposed in a housing at atmosphere pressure and located within said container, said device being fluidly connected to said collection chamber and including an indicator member whose movement is proportional to the suction created in the collection chamber.

7. Apparatus as claimed in claim 6 wherein said pressure responsive device comprises a bellows which contracts responsive to an increase in suction and said indicator member comprises an indicator vane coupled to said bellows, said indicating means further comprising a scale which cooperates with said indicator vane to provide an indication of the suction created.

8. Apparatus as claimed in claim 7 further comprising spring means for mounting one end of said bellows to permit expansion and contraction of said bellows, said spring means including a spring connected between the said one end of said bellows and a wall of said container.

9. A surgical drainage apparatus as claimed in claim 1 and further including a one-way valve means located in the fluid path of said negative pressure relief valve means such that upon actuation of said negative pressure relief valve fluids only flow in a direction from said connection means to said fluid inlet.

10. A surgical drainage apparatus as claimed in claim 1 wherein said variable control means includes an elongate tubular body fluidly connected at one end to said collection such that said tubular body comprises said connection means, a plurality of openings located along the length of said tubular body, and a sheath means for covering said openings and which is longitudinally movable along said tubular body to uncover a select number of said openings so as to bleed air to the suction source to incrementally control the suction within said collection chamber.

11. A surgical drainage apparatus as claimed in claim 10 wherein said tubular body is attached to said container and is provided with an external threaded portion, and wherein said sheath has a central bore containing an internal threaded portion mating with said external threaded portion of said tubular body such that said sheath is threadably received on said tubular body and is rotated in one direction to longitudinally move said sheath to incrementally uncover said openings and is rotated in the other direction to incrementally cover said openings.

12. A surgical drainage apparatus as claimed in claim 11 wherein said tubular body further includes a stop means for preventing said sheath from moving to a position where all of said openings are covered.

13. A surgical drainage apparatus as claimed in claim 11 wherein the other end of said tubular body includes a restricted passageway such that fluid flow to the suction source is restricted.

14. A surgical drainage apparatus as claimed in claim 11 wherein a one-way valve means is provided between said collection chamber and said one end of said tubular body for allowing fluid flow only from said collection chamber to said tubular body.

15. A surgical drainage apparatus as claimed in claim 14 and further including a housing located at said one end of said tubular body in which said one-way valve means is located, said housing including a well at the bottom thereof such that where said container is tipped allowing liquids to enter said housing, a portion of the liquids enter said well and serves to indicate that said container has been tipped.

* * * * *